United States Patent [19]

Reimels

[11] 4,118,805
[45] Oct. 10, 1978

[54] ARTIFICIAL SPHINCTER
[75] Inventor: Harry G. Reimels, Braintree, Mass.
[73] Assignee: Codman & Shurtleff, Inc., Randolph, Mass.
[21] Appl. No.: 773,085
[22] Filed: Feb. 28, 1977
[51] Int. Cl.² .......................... A61F 1/00; A61B 17/00
[52] U.S. Cl. ........................................... 3/1; 128/1 R; 128/346; 128/DIG. 25
[58] Field of Search ............... 3/1; 128/1 R, DIG. 25, 128/346

[56] References Cited
U.S. PATENT DOCUMENTS

| | | | |
|---|---|---|---|
| 2,921,584 | 1/1960 | DiVette | 128/346 |
| 3,744,063 | 7/1973 | McWhorter et al. | 3/1 |
| 3,863,622 | 2/1975 | Buuck | 128/DIG. 25 |

FOREIGN PATENT DOCUMENTS 1,174,814  12/1969  United Kingdom ............ 128/DIG. 25

OTHER PUBLICATIONS

"Treatment of Cord Bladder Incontinence in Children" by O. Swenson et al, Annals of Surgery, vol. 144, No. 3, 1956, pp. 421–427.
"Internal Device for Control of Urinary Incontinence" by O. Swenson, Journal of Pediatric Surgery, vol. 7, No. 5, Oct.-Nov. 1972, pp. 542–545.

Primary Examiner—Ronald L. Frinks
Attorney, Agent, or Firm—Richard J. Rodrick

[57] ABSTRACT

An improved artificial sphincter for occluding a duct. The basic sphincter includes means to increase the occlusive force about the duct and means to control the increase of such occlusive force. To protect the duct from excessive or damaging occlusion the basic sphincter is improved by including means for preventing increase of the occlusive force about the duct beyond a predetermined position. An additional improvement includes means for adjusting the occlusive means after the sphincter has been implanted in a human or animal body to account for variations in fit about different ducts.

9 Claims, 9 Drawing Figures

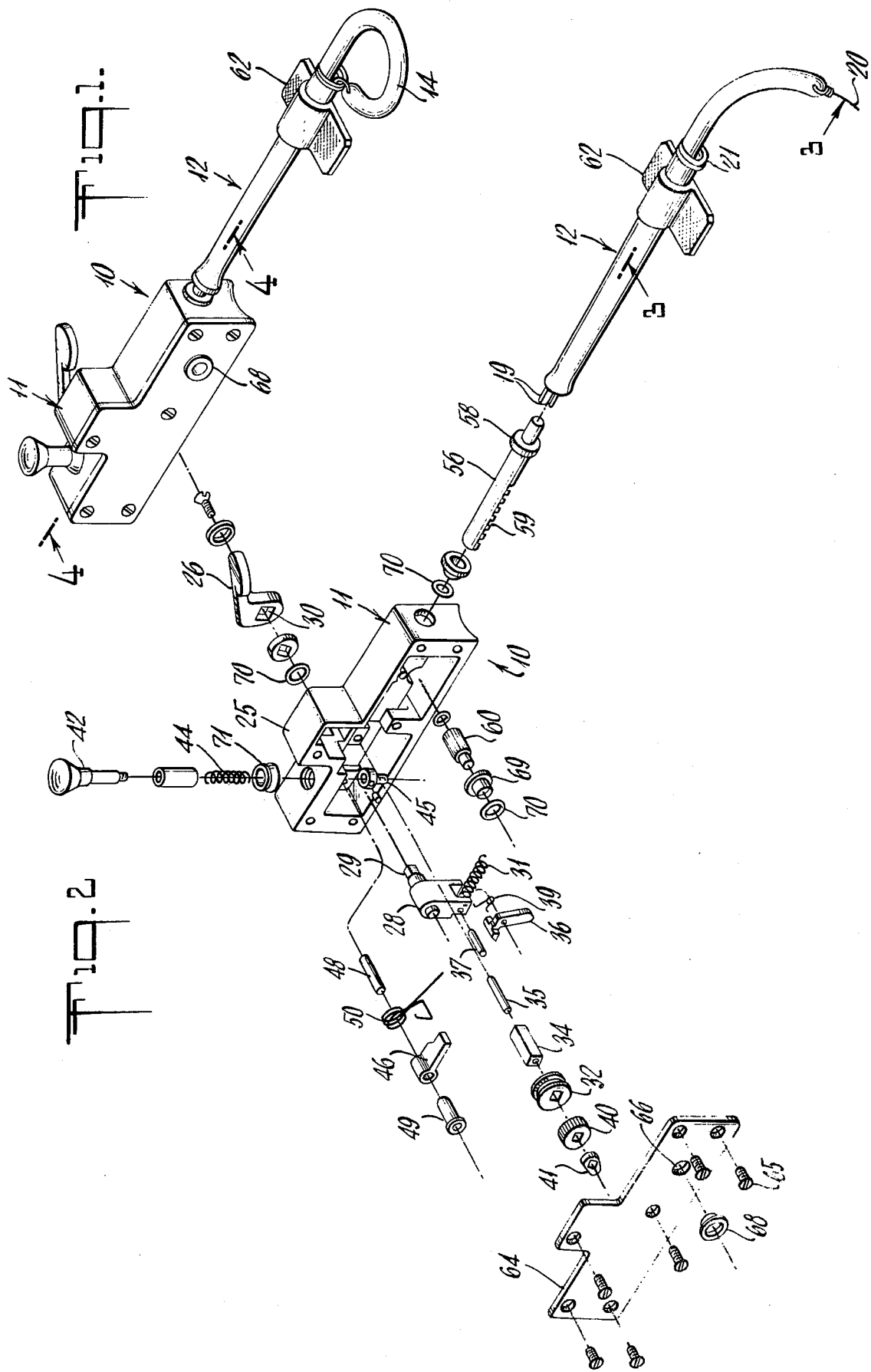

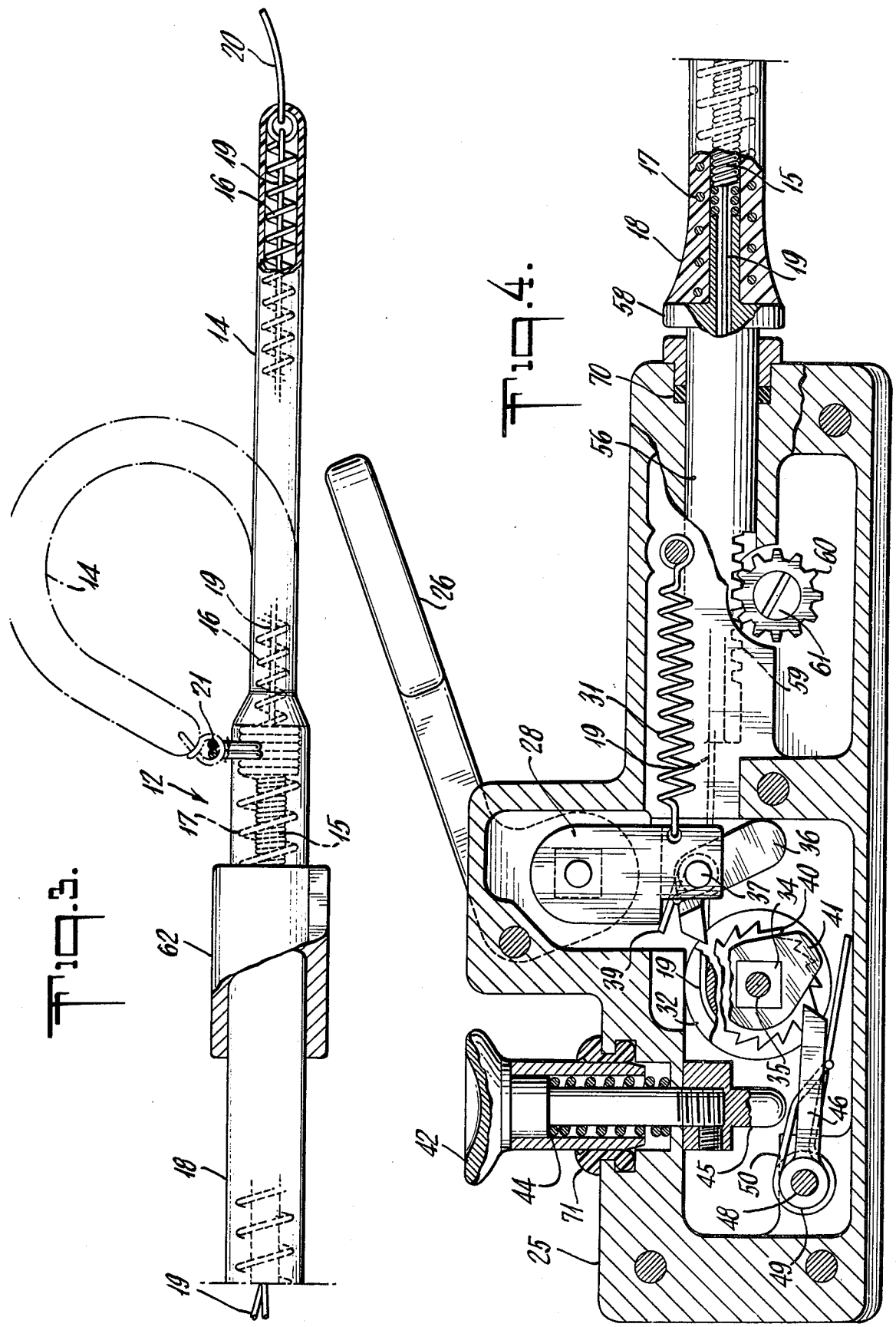

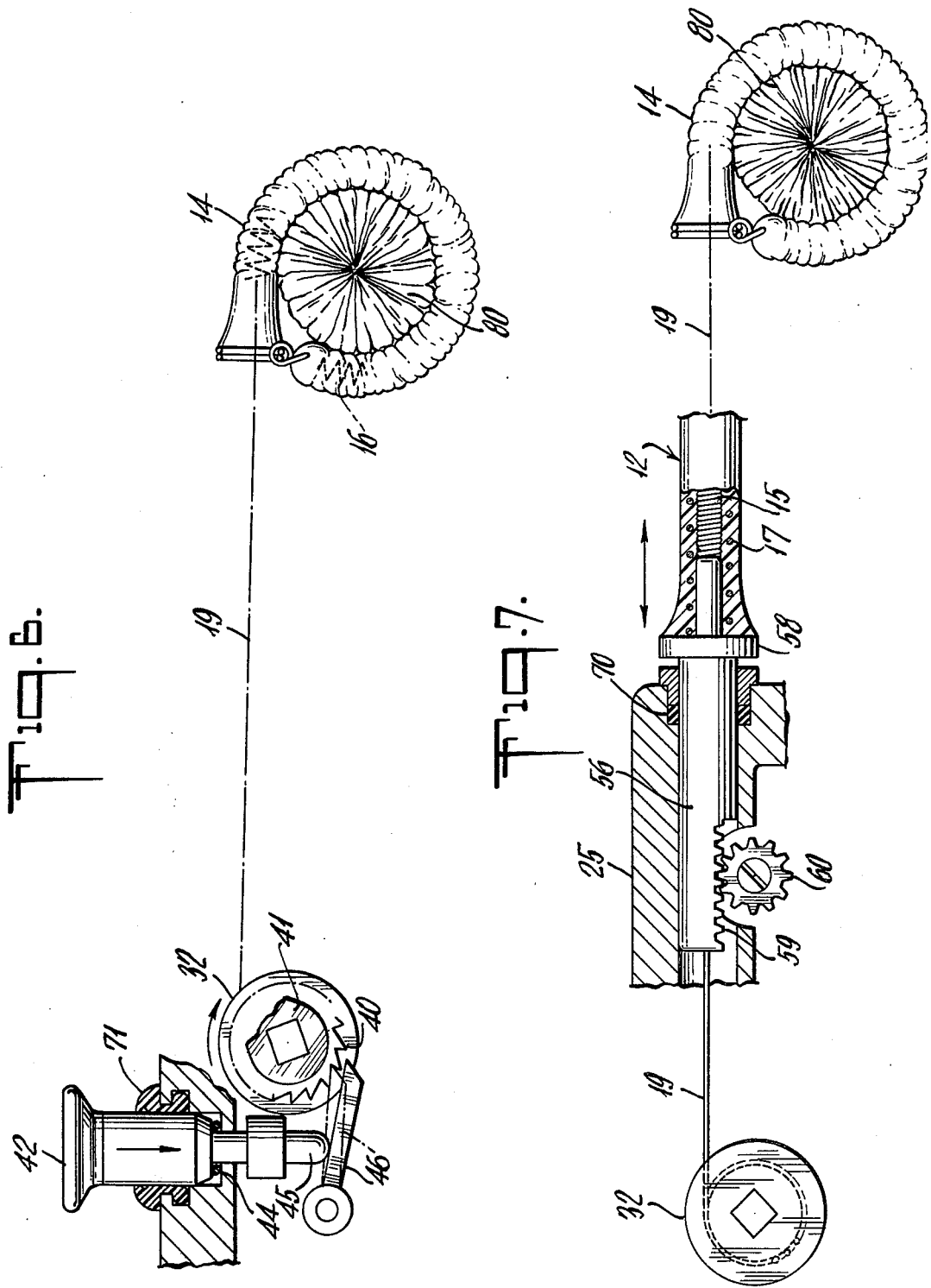

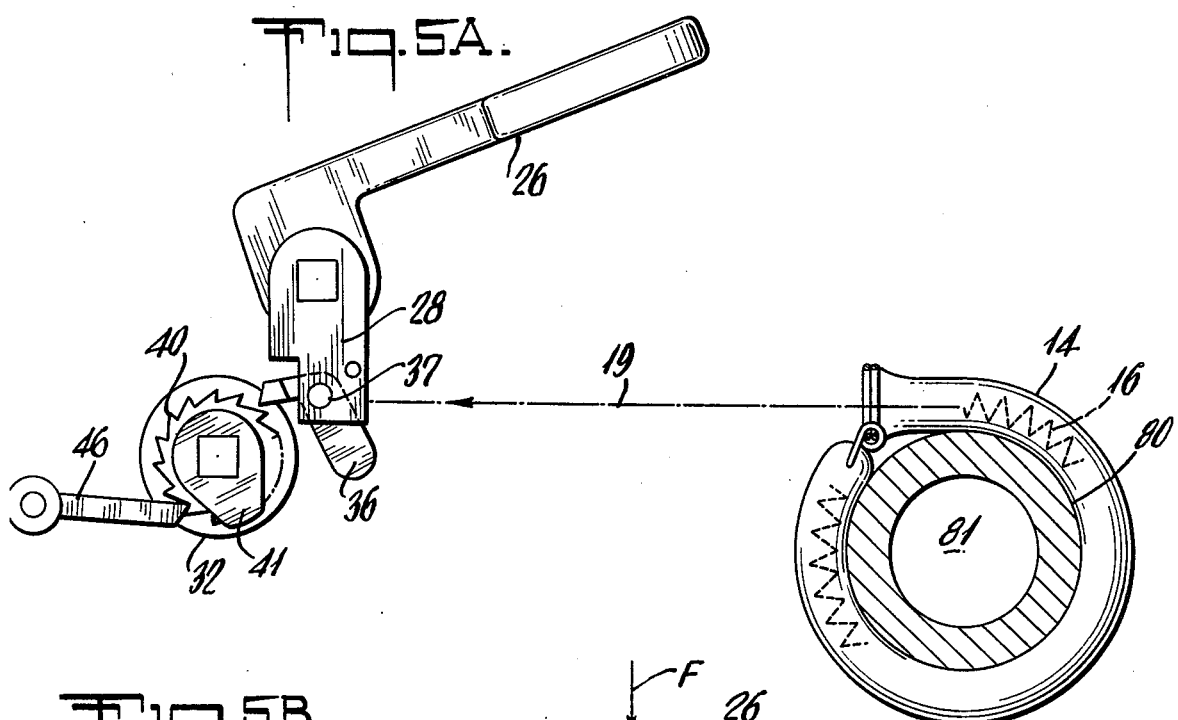
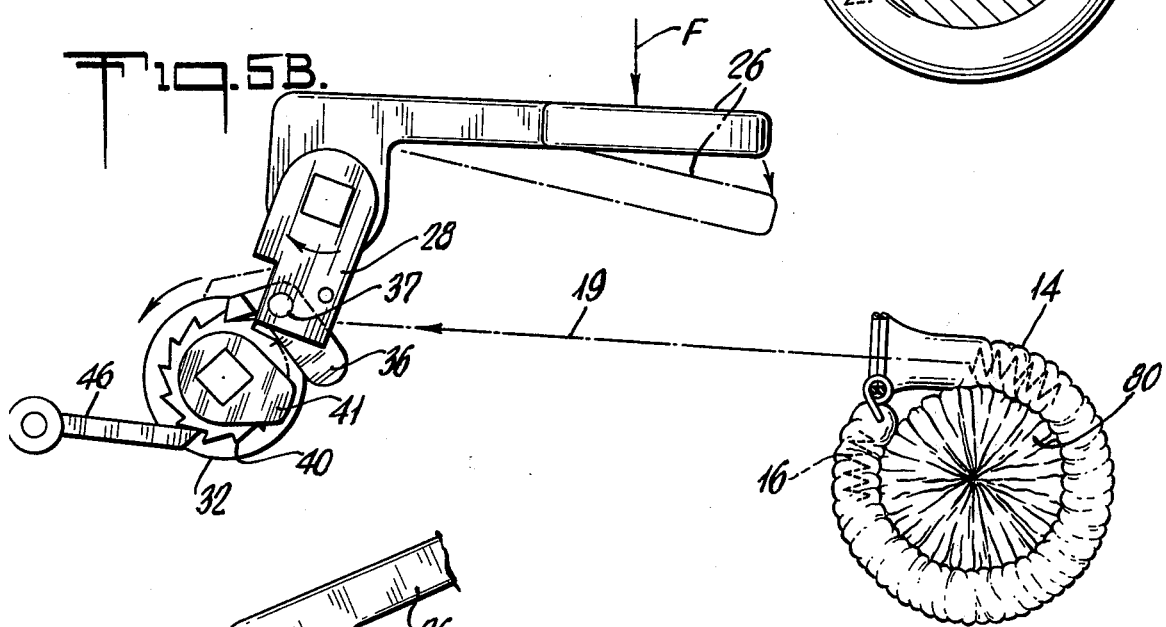
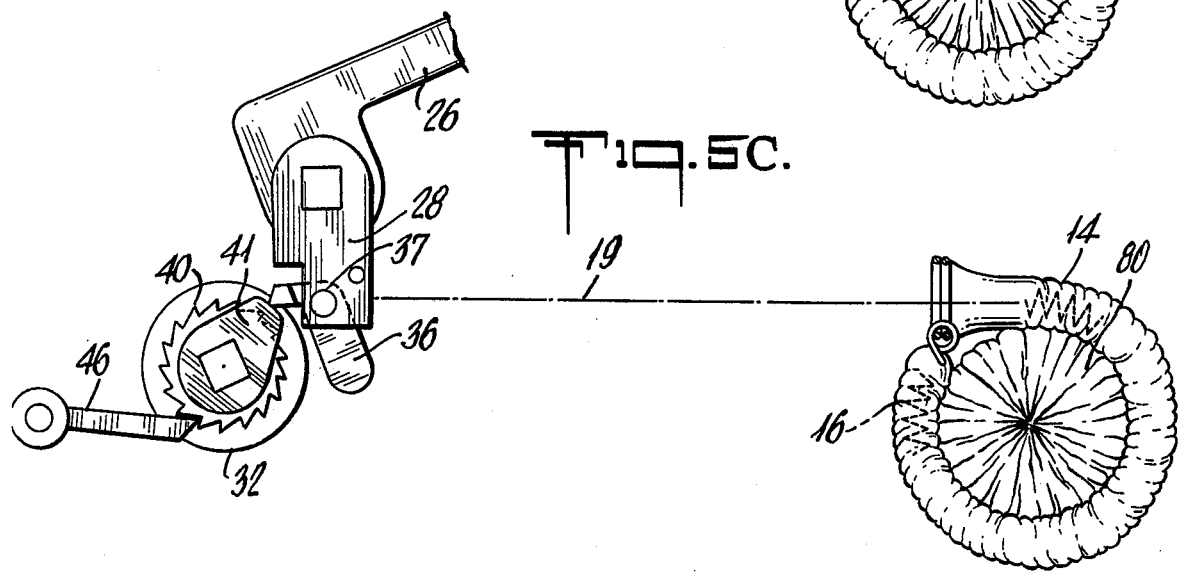

ARTIFICIAL SPHINCTER

BACKGROUND OF THE INVENTION

This invention relates generally to devices for occlusion of ducts, and more particularly concerns an artificial sphincter for use inside a human or animal body as a substitute for a natural sphincter, and whose purpose is to contract a bodily opening or duct and release the same for passage of fluid material therethrough.

Occlusive muscles, such as the sphincter, perform various functions in the human or animal body. One of these muscles, the urinary sphincter, controls the passage of urine from the bladder through the urethral duct. When the urinary sphincter malfunctions, is surgically removed or is impaired for other reasons, control of the flow of urine through the urethra is lost thereby producing a situation of incontinence. Various drainage devices, diaper type collectors and urinal attachments have been used to assist persons having urinary incontinence. Those items, while helping make life more routine for such persons, do not affect the source of the problem, namely the lack of muscular control of the urethra. Lately, however, a number of solutions have been proposed as substitutes for the natural sphincter, to control the flow of urine through the urethral duct, thereby eliminating the need for extra urinary attachments or assists.

A pneumatic sphincter was conceived by Dr. Orvar Swenson by 1956 (*Annals of Surgery*, Vol. 144, No. 3, Sept. 1956). In that device, an inflatable cuff surrounds the urethra such that voluntary inflation of the cuff prevents the escape of urine through the urethra. Deflation of the cuff opens the urethra to permit bladder emptying. Such a device is implanted outside of the urinary system, however, to prevent infection. Additionally, means for injecting air into the inflatable cuff at periodic intervals is often impractical and cumbersome and may be inconvenient for the user.

In 1972 Dr. Swenson proposed another device which under mechanical control would successfully produce urinary control (*Journal of Pediatric Surgery*, Vol. 7, No. 5 (Oct-Nov.), 1972). This latest mechanical device of Dr. Swenson offers a number of significant features that results in a very practicable and advantageous product. Following are some of the noteworthy features:

1. Although implanted inside a human or animal body, the mechanical sphincter is outside the urinary system, thereby eliminating or reducing the possibility of infection;
2. The control mechanism is activated by pressure applied through the skin to tighten and release the device;
3. Pressure on the skin over the control fully releases urethral compression to provide a completely unobstructed urethra;
4. The device is implanted completely under the skin; and
5. Pressure on the urethra produced by such a device does not cause stricture or necrosis.

This type of device not only successfully occludes the urethral duct to prevent escape of urine and releases the duct to allow urine flow, but also is conveniently and voluntarily operable by the person having need for such a device. While the advantages of the artificial mechanical sphincter proposed by Dr. Swenson are highly commendable, there are a few shortcomings in its design and function which have been noted.

To occlude the urethral canal the sphincter includes a control mechanism to tighten the diameter of a coil or torus circumferentially located about the urethra. In operation the control mechanism incrementally tightens the coil by voluntary pressure by the user until escape of urine is prevented. However, there is no limit to the tightening level of the control mechanism so that excessive tightening of the coil is permitted which would inflict damage to the urethra. Excessive tightening could be problematical especially in situations where the device is implanted in children, for example. Another problem involves the adjustment of the sphincter after it has been implanted in a body. For instance, after a period of time and use of the sphincter some dribbling may occur. Further tightening by the control mechanism may be uncomfortable or damage the urethra canal. To adjust the tightening coil to overcome this problem often requires an additional surgical or hospital visit so that the surgeon can gain access to the implanted sphincter to perform the necesary adjustments.

Another artificial sphincter is disclosed in British Pat. Specification No. 1,174,814. That spincter includes a pneumatically, hydraulically, mechanically or electrically operable occluding body directly or indirectly connected with operating means for causing movement of the body to close or release the duct.

SUMMARY OF THE INVENTION

The improved artificial sphincter of the present invention includes all the features of Dr. Swenson's basic concept and provides a number of improvements to overcome the deficiencies in the basic sphincter as pointed out above. In the present invention the improvement concerns the prevention of occlusion of the urethral or other duct beyond a level which would be excessive or damaging to the duct. By incorporating this improved feature in the sphincter, a certain level of tightening about the duct can be accomplished to prevent escape of fluid through the duct, but regardless of how often the control mechanism is activated a certain level of tightening cannot be exceeded. Thus, inadvertent or unnecessary damage to the occluded duct is avoided.

In addition, a further improvement in the basic sphincter includes an adjustment of the occluding or tightening means about the duct. This adjustment feature is available after the improved sphincter has been implanted in a human or animal body and is especially helpful in accommodating variances in fit around different ducts. Moreover, the preferred adjusting means is accessible merely by puncturing the skin with a sharp instrument, and using only a screwdriver, instead of a complete surgical operation in which the adjustor requires the entire sphincter to be exposed before him.

In accordance with the principles of this invention, an artificial mechanical sphincter, for implantation within a human or animal body, has been improved. This improved sphincter includes means for occluding a duct and means for increasing the occlusive force by tightening the occlusive means about the duct. To mechanically control the increase of occlusive force means associated with the force increasing means is provided. Means responsive to an urging movement releases the occlusion of the duct. To improve this spincter there is provided means for preventing the increase of the occlusive force beyond a predetermined tightening position to protect the duct from excessive or damaging occlusion.

In the preferred embodiment of the improved sphincter the means for preventing increase of the occlusive force includes a cam mechanism engageable with an activating pawl used to tighten the occlusive means about the duct. The lobe of the cam, when engaging the activating pawl, lifts the latter so that further activation of the pawl is prevented as is additional tightening of the occlusive means about the duct.

An additional improvement in the sphincter of this invention concerns means for adjusting the occlusive means after the spincter has been implanted in a human or animal body to accout for variations in fit about the duct. For example, in the preferred embodiment use of a rack and pinion is so constructed in the sphincter so that the means to occlude the duct may be adjusted to make it slightly tighter or slightly looser after the implantation of the sphincter has been completed.

BRIEF DESCRIPTION OF THE DRAWINGS

These and other advantages, features and aspects of the invention will become apparent upon reading the following detailed description and upon reference to the accompanying drawings, in which:

FIG. 1 is a perspective view of the preferred embodiment of this invention;

FIG. 2 is an exploded view of the embodiment of FIG. 1;

FIG. 3 is a sectional view through lines 3—3 of FIG. 2;

FIG. 4 is a sectional view taken along lines 4—4 of FIG. 1;

FIG. 5a is an elevational view of the drum winding mechanism with no cable tension;

FIG. 5b is an elevational view of the drum winding mechanism activated to shorten the cable length;

FIG. 5c is an elevational view of the drum winding mechanism illustrating the preventative occlusion tightening feature;

FIG. 6 is a partial elevational view illustrating the occlusion release feature; and FIG. 7 is a partial elevational view illustrating the effect of adjustment on the occlusive ring.

While the invention will be described in connection with a preferred embodiment, it is understood that it is not intended to limit the invention to that embodiment. On the contrary, it is intended to cover all alternatives, modifications, and equivalents as may be included within the scope and spirit of the described invention.

DETAILED DESCRIPTION OF AN EXEMPLARY EMBODIMENT

Adverting to the drawings wherein the preferred embodiment of the present invention is illustrated, there is shown an improved artificial mechanical sphincter 10. While the invention may at times be described in conjunction with its use as an artificial urinary sphincter for control of urinary incontinence it is understood that this is merely for descriptive purposes and the invention in its application is not so limited. For example, this artificial sphincter may have use in conjunction with intestinal ducts, with the bowels or in the correction of anorectal problems. This sphincter is composed primarily of two subassemblies, housing subassembly 11, and torus or ring subassembly 12. Torus subassembly 12 as seen in FIG. 1 includes a looped flexible member 14 which is capable of being adjusted to change the diameter formed by the loop. It is this loop 14 which is placed about the duct so that passage of fluid can be controlled or prevented as necessary. The construction of the torus assembly 12 is more clearly illustrated in FIG. 3 with its looped member 14 depicted in a straight lying condition for clarity.

Inside of the torus subassembly 12 is a tight wound compressible spring 15 in that section before the looped member 14. The spring has been expanded to form a compression spring 16 inside the looped portion 14 of the torus subassembly. This spring, both compressible and incompressible portions, is preferrably encased in a silicone or like tubing over which another spring 17, generally noncompressible but bendable, is placed to provide flexibility to this subassembly of the sphincter. Encasing the entire spring assembly is preferably a silicone adhesive coating 18 which is flexible and smooth to provide a level of comfort to the duct around which it is used. Connected to the distal end of the compressible spring 16 at one end of the loop 14 is a cable 19 which extends through the spring 16 and the entire torus subassembly 12 for attachment inside the housing subassembly 11 as hereinafter described. Cable 19 may have one or more passes throughout the torus subassembly, more than one cable pass providing the flexibility of thinner individual cables versus one of heavier construction. To form the looped portion 14, the compressible spring section is flexed to encircle the duct and the loop is completed by affixing suture 20 or other suitable means to ring 21 located near the point where the incompressible portion 15 of the spring and compressible portion 16 of the spring meet. Once this loop or torus has been formed the occlusion and release of the duct can be performed.

Referring particularly to FIGS. 2 and 4, the contents of the housing subassembly 11 are seen. Attached to housing 25 is a depressible lever 26, generally having an area thereon to be depressed by a thumb or finger. Actuator 28 is mounted inside housing 25 and a peg 29 thereon is inserted into a corresponding opening 30 in lever 26 so that rotative movement or depression of the lever 26 will also rotate actuator 28; to maintain depressible lever 26 in its upward or starting position a spring 31 keeps actuator 28 under tension. After lever 26 is depressed and finger pressure is released, spring 31 will lift the lever back to its starting position.

Inside housing 25 is a drum 32, generally having flanges along the edges thereof similar to a spool. Shafts 34 and 35 connect drum 32 to the housing thereby providing its rotative ability. As hereinafter discussed drum 32 acts as a wind-up mechanism for the cable 19 of the torus subassembly. At the lower portion of the actuator 28 activating pawl 36 is pivotally attached by means of shaft 37 and held in spring tension by actuating pawl spring 39. Actuating pawl 36 is positioned inside the housing so as to be engageable with a ratchet 40 which is located adjacent drum 32. Since shaft 34 is common to both the ratchet 40 and drum 32 it is seen that rotative movement of the ratchet produces a corresponding rotation of the drum 32. Also attached to common shaft 34 is a cam 41, which rotates with ratchet 40 and is positioned so that the lobe of the cam can engage activating pawl 36 after the cam rotates a sufficient amount.

As a means to release the occlusive force about a dust a finger depressible release pin 42 is affixed to housing 25 with a compression spring 44 providing a spring-loaded return of the pin after finger pressure is removed therefrom. The bottom portion 45 of pin 42 descends into the housing and is located near locking pawl 46, which is pivotally attached to the housing by means of shaft 48 and bushing 49 with locking pawl spring 50 providing spring tension. As seen especially in FIG. 4 locking pawl 46 is positioned adjacent ratchet 40 so as to engage the teeth thereof and maintain each incremental rotative step of the ratchet and drum.

Slidably mounted in an end of housing 25 is a rack 56 generally positioned so that one end 58 thereof remains outside of the housing; in the embodiment being described the teeth 59 of the rack are oriented in a downward position. Engaged in gear contact with the teeth 59 is a pinion 60 generally having a screw slot 61 so that the pinion may be turned by a screwdriver or like tool. It can be seen that rotating the pinion 60 will provide lateral movement to rack 56 thereby sliding the same in or out depending upon rotative direction of the pinion. To end 58 of the rack is attached one end of the torus subassembly 12 by silicone adhesive or other various means of making this attachment. Cable 19 in the torus subassembly extends through the rack 56 and terminates at the drum 32 where it is wound during tightening of the occlusive torus. Suturing sleeve 62 is provided on the torus subassembly 12 for purposes of fastening the sphincter torus in position after implantation in a human or animal body.

Housing 25 is appropriately closed by a cover 64 with convenient hardware such as screws 65. An opening 66 is provided in cover 64 for access to pinion 60 inside the housing. Pinion ring 68 and collar 69 locate the pinion with respect to opening 66 while O-ring 70 maintains a positive seal around the opening. It is noted that an O-ring is also used to seal the openings associated with the slidable rack 56 and the depressible lever 26, while release seal 71 is used in conjunction with the depressible release pin 42.

To understand the relationship between the lever mechanism and the occlusive torus, and the advantage realized by one of the improvements of this invention, attention is directed to FIGS. 5a, b, and c. In FIG. 5a, torus loop 14 encircles a duct 80, such as the urethra, with the opening 81 in the duct remaining unconstricted so that fluid can pass therethrough. It is noted that compression spring 16 is in its expanded condition. Cable 19 passes out through the looped torus 14 to the wind-up drum 32 (the housing and other elements have been deleted for clarity sake). Activating pawl 36 is positioned to be engageable with the teeth of ratchet 40, while locking pawl 46 is locked into the ratchet teeth to prevent, in this instance, clockwise rotation of the ratchet. It is noted that the lobe of cam 41, at this stage of the tightening process, is directed away from activating pawl 36 and is not making contact with the same. Depressible lever 26 is in the upward or starting position when no finger force is being applied.

Turning now to FIG. 5b, finger force F applied to lever 26 depresses the same downward and through actuator 28 forces activating pawl against the teeth of ratchet 40 to produce an incremental rotative movement in the counterclockwise direction. This, of course, also rotates the drum 32 whereby cable 19 is wound around drum 32. The effect of this cable winding shortens the length of cable 19 inside the torus looped member 14; by shortening cable 19 the spring 16 therein is compressed with the result that the looped diameter of the torus 14 becomes smaller. Each depression of lever 26 tightens the diameter of the loop around duct 80 until the opening therein is completely restricted as seen in FIG. 5b. The restriction of the duct is maintained by the locking action of pawl 46 on the teeth of the ratchet 40 each time the lever 26 returns to its starting position and the activating pawl 36 becomes disengaged from the ratchet 40.

Without the improved features of this invention, it can be seen that the cable shortening mechanism may constrict the opening in the duct to such an extent that damage will result. The improvement in this regard is illustrated in FIG. 5c wherein it is noted that the lobe of cam 41 has rotated, in this instance, counterclockwise in incremental steps with each movement of the ratchet 40. Cam 41 is shown engaging the activating pawl 36 so that when lever 26 is depressed the activating pawl is lifted to prevent further cooperation with the ratchet 40. As a result, further tightening of cable 19 is prevented with a limitation on the amount that loop 14 is tightened to protect duct 80 from excessive or damaging occlusion. When assembling cam 41 to the ratchet 40 it is positioned to allow a predetermined number of rotative movements of the drum before the cam lobe engages the activating pawl 36. This way, sufficient restrictive tightening of the duct 80 can be achieved, but excessive tightening is prevented.

When it becomes necessary to allow fluid to pass through the duct opening, such as from the bladder through the urethra, the user of the sphincter merely has to depress release pin 42 a sufficient depth to contact the locking pawl 46 which maintains the cable 19 in tension. In FIG. 6 the release pin depression is illustrated whereupon the urging movement of pin portion 45 against locking pawl causes disengagement from the teeth of the ratchet 40. The effect of this disengagement is to allow the drum to turn clockwise under the decompression of spring 16 in the looped member 14. Concurrently therewith, cable 19 lengthens and the diameter of loop 14 increases, releasing the occlusion of duct 80 and allowing fluid to pass through opening 81.

Another improvement of the present invention is more clearly illustrating in FIG. 7. At times when the duct 80 is occluded and after some use, slight dribbling through the opening may occur. An additional incremental step of the ratchet may overcompensate for this dribbling by either causing discomfort to the patient or damaging the duct. In these situations minor adjustments of the occlusive diameter of the looped member 14 are extremely valuable. These adjustments are accomplished by rotating pinion 60 by means of a screwdriver or like tool. Rotation of pinion 60 slides rack 56 laterally to produce an inward or outward movement of the rack with regards to the housing 25. As cable 19 is wound around drum 32 and its length is thereby fixed, slight movements of rack 56 will produce a slight alteration of the length of the flexible torus loop 14. For instance, rotation of pinion 16 counterclockwise draws the rack 56 inward thereby increasing the diameter of looped member 14 while leaving cable 19 length constant; rotating pinion 60 clockwise produces the opposite effect, namely a slight reduction of the diameter formed by loop 14.

As a means of producing urinary continence and control over the passage of urine from the bladder the improved artificial sphincter of the present invention is completely implanted in the human body. The sphincter is located in the area of the lower abdomen directly under the skin and is oriented so that the occlusive torus may encircle the urethra. To use this device the person merely manipulates the depressible lever through the skin to produce the necessary occlusive or restrictive force to prevent urine from escaping. With the improvements of the present invention the person does not have to worry about excessive tightening of the occlusive ring. When this person has to empty the bladder, the release pin is merely depressed, once again through the skin with the resultant release of occlusive force about the urethra and passage of the urine therethrough. In those situations where a minor adjustment is required, especially after use of the sphincter or in situations where variations in fit about the duct are required, the adjusting pinion is readily accessible. As the entire sphincter is directly beneath the surgeon can perform the adjustment by a slight puncture wound to allow the tool to reach and rotate the pinion in the required direction. Thus, no complicated surgical operation is required to perform the minor adjustments which often are needed.

Inasmuch as the entire sphincter is to be implanted in the body, the materials used should be bio-compatible. While medical grade titanium alloy is preferred other material such as medical grade stainless steel, cobalt-chrome alloy, high molecular weight plastics and other materials commonly acceptable for use inside the human body may be utilized. In the embodiment wherein the sphincter is used for urinary incontinence, the typical size of the housing is 2.5 by 1 by 0.5 inches (6.2 by 2.5 by 1.2 cm.); a typical torus assembly is approximately 2 inches (5 cm.) long (extended length), while the diameter is about 0.6 inches (1.5 cm.).

Thus, it is apparent that there has been provided in accordance with the invention an improved artificial mechanical sphincter that fully satisfies the aims, advantages and aspects as set forth above. While the invention has been described in conjunction with specific embodiments thereof, the plenary invention is intended to embrace all alternatives, modifications and variations which will be apparent to those skilled in the art in view of the foregoing description and which fall within the broadest scope and spirit of the described invention.

What is claimed is:

1. In a non-inflatable artificial mechanical sphincter of the type for implantation within a human body, said sphincter having means for occluding a duct; adjustable spring means associated with said occlusion means for increasing an occlusive force around said duct; means associated with said spring means to mechanically control said increase of occlusive force; and means responsive to an urging movement for releasing occlusion of said duct, wherein the improvement comprises: means for preventing increase of said spring means beyond a predetermined tightening position to protect said duct from excessive or damaging occlusion.

2. An artificial sphincter as defined in claim 1 wherein said means for occluding a duct includes a looped flexible member capable of being adjusted to change the diameter formed by said loop, thereby changing said occlusive force about said duct.

3. In an artificial mechanical sphincter of the type for implantation within a human body, said sphincter having means for occluding a duct including a looped flexible member capable of being adjusted to change the diameter formed by said loop, thereby changing said occlusive force about said duct, one end of said looped member being attached to a housing, said looped member including a compressible spring therein extending substantially the entire looped dimension; means for increasing an occlusive force about said duct by tightening said occlusive means including a cable connected to the distal end of said spring, extending therethrough, and connected to a wind-up drum located in said housing, whereby winding said drum in one direction shortens the length of said cable, compresses said spring and reduces the diameter of said looped member, then winding said drum in the opposite direction lengthens said cable decompresses said spring and increases said looped diameter about said duct; means associated with said force increasing means to mechanically control said increase of occlusive force; and means responsive to an urging movement for releasing occlusion of said duct, wherein the improvement comprises: means for preventing increase of said occlusive force beyond a predetermined tightening position to protect said duct from excessive or damaging occlusion.

4. An artificial sphincter as defined in claim 3 wherein said means associated with said force increasing means to mechanically control said increases of occlusive force includes a depressible lever attached to said housing under spring tension and being responsive to an applied finger force and means connecting said lever to said drum so that depression of said lever rotates said drum thereby shortening said cable and tightening said flexible loop.

5. An artificial sphincter as defined in claim 4 wherein said means connecting said lever to said drum includes a ratchet associated with said drum and an activating pawl located adjacent to said ratchet for engagement therewith, said activating pawl being responsive to the depressive movement of said lever to incrementally drive said ratchet and drum in a rotative movement; and further includes a locking pawl located adjacent said ratchet to maintain each incremental rotative movement of said ratchet and drum while said lever is in the non-depressed, starting position and said activating pawl is disengaged from said ratchet; and wherein said means for preventing increase of said occlusive force includes a cam rotatable with said drum, the lobe of said cam being engageable with said activating pawl to lift the same so that further cooperation of said activating pawl with said ratchet is prevented, said lobe being rotatably positioned to allow a predetermined number of incremental rotative movements of said drum before engagement of lobe and activating pawl occurs thereby fixing the amount said cable may be shortened and said looped tightened to protect said duct from excessive or damaging occlusion.

6. An artificial sphincter as defined in claim 5 wherein said means for releasing occlusion of said duct includes a springloaded, finger depressible release pin having a portion thereof located adjacent said locking pawl for contact therewith, whereby sufficient depression of said pin causes contact between said pin and said locking pawl and urges said locking pawl to become disengaged from said ratchet, thereby allowing said spring in said loop to decompress and said loop diameter to increase and release occlusion of said duct.

7. In an artificial mechanical sphincter of the type for implantation within a human body, said sphincter having means for occluding a duct; means for increasing an occlusive force about said duct by tightening said occlusive means; means associated with said force increasing means to mechanically control said increase of occlusive force; and means responsive to an urging movement for releasing occlusion of said duct, wherein the improvements comprise: means for preventing increase of said occlusive force beyond a predetermined tightening position to protect said duct from excessive or damaging occlusion, and means for adjusting said occlusive means after said sphincter has been implanted to account for variations in fit about said duct.

8. An artificial sphincter as defined in claim 7 wherein said means for occluding a duct includes a looped flexible member capable of being adjusted to change the diameter formed by said loop; a compressible spring in said looped member extending substantially the entire looped dimension; and a cable connected to the distal end of said spring, extending therethrough, and terminating outside of said loop and inside a housing located adjacent to said loop; said occlusion adjusting means being provided by having one end of said flexible loop attached to a rack slidably mounted in said housing; a pinion mounted in said housing in gear contact with said rack, said pinion including means thereon for rotating the same, whereby rotation of said pinion slides said rack to vary the overall length of said looped member but leaves the length of said cable inside said looped member constant thereby adjusting the diameter formed by said loop.

9. An artificial sphincter as defined in claim 8 wherein said means for rotating said pinion is a screw slot in said pinion to accommodate a screwdriver tool for making said adjustments.

* * * * *